United States Patent [19]

French et al.

[11] Patent Number: 4,818,436

[45] Date of Patent: Apr. 4, 1989

[54] PROCESS AND COMPOSITION FOR PROVIDING REDUCED DISCOLORATION OF PYRITHIONES

[75] Inventors: Cheryl B. French, Glastonbury; Gene A. Hyde, Hamden, both of Conn.

[73] Assignee: Olin Corporation, Cheshire, Conn.

[21] Appl. No.: 91,684

[22] Filed: Aug. 31, 1987

[51] Int. Cl.[4] .................. C07C 143/90; C11D 1/28
[52] U.S. Cl. ................................. 252/400.23
[58] Field of Search ............... 514/108, 188, 970, 852; 252/400.2, 400.23

[56] References Cited

U.S. PATENT DOCUMENTS

| | | | |
|---|---|---|---|
| 2,809,971 | 10/1957 | Bernstein et al. | 260/270 |
| 3,159,640 | 12/1964 | McClure et al. | 260/294.8 |
| 3,899,293 | 8/1975 | Bush | 252/400.23 |
| 4,533,736 | 8/1985 | Trotz et al. | 546/290 |
| 4,557,896 | 12/1985 | Brocklebank et al. | 252/400.23 |

FOREIGN PATENT DOCUMENTS 77630 4/1983 European Pat. Off. ............ 514/188
2262375 6/1974 Fed. Rep. of Germany .

OTHER PUBLICATIONS

Chem. Abst. 73:37188(a) (1970)–Jacques.
Technical Bulletin No. IC/SCS-323, "DEQUEST® 2001 Phosphonate; for Scale and Corrosion Control, Chelation, Dispersion", St. Louis, Mo., from Monsanto Industrial Chemicals Company, pp. 1-5.

Primary Examiner—Douglas W. Robinson
Attorney, Agent, or Firm—Dale Lynn Carlson

[57] ABSTRACT

Aqueous pyrithiones and a process and composition for providing reduced discoloration of these pyrithiones using an alkali metal or alkaline earth metal salt of 1-hydroxyethane-1,1-diphosphonic acid.

13 Claims, No Drawings

PROCESS AND COMPOSITION FOR PROVIDING REDUCED DISCOLORATION OF PYRITHIONES

FIELD OF THE INVENTION

This invention relates generally to aqueous pyrithiones and, more specifically, to a process and composition for providing reduced discoloration of these pyrithiones in the presence of ferric ion.

DESCRIPTION OF THE PRIOR ART

Sodium pyrithione [also called the sodium salt of 1-hydroxy-2-pyridinethione, sodium pyridine-2-thiol-N-oxide, or 2-pyridinethiol-1-oxide, Na salt] is typically employed as a biocide and preservative in fuctional fluids, such as metalworking fluids, lubricants, cosmetics and toiletries.

Likewise, zinc pyrithione [also known as zinc pyridine-2-thiol-N-oxide or bis[1-hydroxy-2(H)pyridinethionato]-zinc] is an excellent biocide. It has been employed as a broad-spectrum anti-microbial agent and preservative in metalworking fluids, plastics, and cosmetics. Its principal uses are as an anti-dandruff agent in hair products or as a preservative in various cosmetics and toiletries.

Since the aesthetics of metalworking fluids, cosmetics and toiletries normally require certain desirable colors, and the formulators of such products go to great lengths to achieve specific color effects, any ingredient which causes the functional fluid to vary much from white or colorless may take the colorant formulators' task very difficult.

In the presence of ferric ion, pyrithione-containing compositions tend to turn blue even though the ferric ion is present in mere trace amounts. This blue discoloration is undesirable for aesthetic reasons, as discussed above.

In addition to the aesthetics problems, the blue coloration problem associated with the presence of ferric ion causes a funtioning problem in the pyrithione-containing compositions. This problem results from the fact that the pyrithione tends to form a blue precipitate in the presence of ferric ion. The precipitate reduces the amount of available pyrithione available throughout the composition, thereby diminishing the biocidal protection thereof.

Various additives for pyrithione-containing functional fluids have been suggested in the past in an attempt to solve the problems associated with discoloration thereof. These additives include EDTA, nitrilotriacetic acid and ethylenediamine tetra(methylene)-phosphonic acid. However, none of these additives are as effective in avoiding or reducing the blue coloration problem associated with ferric ion as might be desired and several exhibit high toxicity.

In view of the above, new approaches to avoiding or reducing the blue coloration problem associated with ferric ion in pyrithione-containing compositions including those with functional fluids, during manufacture and storage thereof, would be highly desired from a commercial standpoint.

SUMMARY OF THE INVENTION

The present invention is directed to a process for preventing or reducing discoloration of aqueous sodium or zinc pyrithione by treating the pyrithione with an effective amount of a selected agent to prevent or reduce the discoloration.

Thus, in one aspect, the present invention relates to a process for reducing or inhibiting the presence of a blue coloration caused by the presence of ferric ion in an aqueous sodium or zinc pyrithione which comprises adding thereto an alkali metal or alkaline earth metal salt of 1-hydroxyethane-1,1-diphosphonic acid (also referred to herein as "HEDP").

In yet another aspect, the present invention relates to a composition free of blue coloration otherwise caused by the presence of ferric ion therein comprising an aqueous sodium or zinc pyrithione and an alkali metal or alkaline earth metal salt of 1-hydroxyethane-1,1-diphosphonic acid.

DETAILED DESCRIPTION OF THE INVENTION

The sodium pyrithione employed in the process and composition of the present invention is a well-known commercial product and is commonly made by reacting 2-chloropyridine-N-oxide with NaSH and NaOH. See U.S. Pat. No. 3,159,640, which issued to McClure on Dec. 1, 1964, incorporated herein by reference.

Zinc pyrithione may be made by reacting 1-hydroxy-2-pyridinethione or a soluble salt thereof with a zinc salt (e.g., $ZnSO_4$) to form a zinc pyrithione precipitate. See U.S. Pat. No. 2,809,971, which issued to Bernstein and Losee on Oct. 15, 1957, incorporated herein by reference.

A wide variety of alkali metal and alkaline earth metal salts of HEDP are useful within the scope of the present invention such as, for example, the sodium, potassium, calcium and magnesium salts of HEDP. Of these, sodium and potassium are preferred. The most preferred salt is potassium based upon its ease of preparation by reacting HEDP with KOH (while cooling the reaction mixture) within a pH range of between about 11 and about 13, more preferably between about 11 and about 12. Below a pH of about 11, precipitation of the $HEDP-K_4$ and/or the pyrithione is frequently encountered, whereas a pH of above about 13 tends tpo cause pyrithione stability problems upon aging of the composition.

In contrast to the ease of preparation of the potassium salt, the sodium salt of HEDP generally requires maintaining the temperature at an elevated level of as high as 90° C. or higher and a pH of between about 10.5 and about 13, preferably between about 11.5 and about 12. Lower temperatures can result in the heavy precipitation of the hydrated trisodium salt of HEDP during the preparation.

Although in its broadest aspect, the present invention encompasses compositions containing only aqueous pyrithione and the above-specified metal salt of HEDP, the invention is advantageously employed with conpositions additionally containing a functional fluid, such as a metalworking fluid. When such a fluid is present, high levels of ferric ion are often encountered. For example, a level of ferric ion of 150 ppm or higher is not uncommon in commercial metalworking fluids. By incorporating an effective amount of the metal salt of HEDP into the composition, the blue coloration attributable to the presence of ferric ion bound with pyrithione is suitably reduced, eliminated, or avoided.

The amount of the above-specified metal salt 1f HEDP incorporated into the compositions of the present invention can vary over a wide range. If the preferred HEDP-K₄ salt is used, the amount of HEDP-K₄ is desirably between about 33 and about 75 weight percent based on the total weight of HEDP-K₄ and pyrithione in the composition. The upper limit on HEDP-K₄ in this range of ratios provides an adequate amount of HEDP-K₄ if the total amount of ferric ion in the composition is no greater than about 150 ppm. If larger quantities of ferric ion are expected to be encountered, the amount of HEDP-K₄ is increased accordingly.

Normally, the preferred composition is supplied as an aqueous concentrate containing a functional fluid, pyrithione, and HEDP-K₄. In the aqueous concentrate, sufficient pyrithione is provided such that the "working" functional fluid will contain a biocidally effective amount thereof. In order to satisfy this requirement, the concentrate for a metalworking fluid, for example, preferably contains between about 450 ppm and about 5000 ppm of pyrithione, thereby providing at least about 45 ppm in the "working" fluid based upon a dilution rate of the concentrate to the "working" fluid of between about 1:10 and about 1:100. Other functional fluids, such as cosmetics, are often formulated directly (without the need for a concentrate) and can contain up to 5000 ppm, or more, for the pyrithione salt. If the composition is pre-determined to have a high ferric ion content, the HEDP-K₄ level can be adjusted accordingly to a higher level as is required to achieve the objective of reduced blue coloration. Alternatively, if periodic influxes of ferric ion are expected to be encountered during use of the composition, such as when using a metalworking fluid that picks up iron during use, periodic or continuous additions of HEDP-K₄ to the fluid can suitablly be made to compensate for the discoloration and loss of microbial effectiveness that would otherwise occur. If significant amounts of calcium or magnesium ions are expected to be present or in the working functional fluid (e.g., caused by the use of hard water to dilute the concentrate), a chelator such as ehtylenediamine tetraacetic acid (EDTA) is suitably utilized in an amount of up to 500 ppm or higher as needed to chelate the calcium or magnesium ions.

Without wishing to be bound by any particular theory, the efficacy of the HEDP-K₄ in preventing or reducing blue coloration in the compositions of the present invention is believed by the present inventors to be attributable to the superior ferric ion binding capability of the above-specified metal salts of HEDP, as compared to the ferric ion binding ability of the pyrithione in the composition. More specifically, since the blue coloration is believed by the instant inventors to be caused by ferric ion bound to pyrithione, blue color elimination or prevention is believed to be effected in accordance with this invention by virtue of the superior ferric ion-binding capability of HEDP-K₄ in competition with the pyrithione present in the composition.

Indeed, some compositions within the scope of the present invention exhibit an initial bluish coloration upon addition of ferric ion. Upon standing for a few minutes, the blue color disappears indicating the effectiveness of ferric ion binding by HEDP-K₄ upon equilibration.

The term "discoloration" as employed herein with respect to pyrithione-containing compositions may mean any unacceptable gray, blue, black, purple or color other than the natural color or desired artificial color of the formulation. It is noted that the natural color of a sodium pyrithione itself is a clear yellow. One way of quantitatively measuring for discoloration in zinc pyrithione is by measuring the Hunter color parameters and calculating a whiteness value from them. Another method is to visually inspect the composition for any signs of off-whiteness, as compared to the desired or white color.

The following examples are intended to illustrate, but in no way limit the scope of, the present invention.

EXAMPLE 1

Efficacy of HEDP-K₄ in Eliminating Blue Coloration Caused by The Presence of Ferric Ion in Pyrithione-Containing Synthetic Metalworking Fluids In order to test the effectiveness of HEDP-K₄ in eliminating or reducing blue color in a pyrithione-containing synthetic metalworking fluid, the following experiments were conducted.

HEDP-K₄ was prepared as follows:

A 60 weight percent aqueous HEDP acid solution was added to a reaction vessel in an amount of 40.2 weight percent based on the weight of this acid plus KOH to be added. The reaction vessel was adequately cooled with an ice bath. Fifty weight percent aqueous KOH in an amount of 59.8 percent by weight based upon the total weight of HEDP plus KOH was added slowly to the reaction vessel containing the HEDP slowly until the pH of neutralization was 12.0.

Various formulations of either the tetrasodium or tetrapotassium salt of HEDP, Sodium Omadine ® (40 weight percent aqueous sodium pyrithione), and, optionally, the tetrasodium salt of EDTA were prepared. The specific formulations (A through F) are described in TABLE I below.

Formulations A through E were then added to a synthetic metalworking fluid in aliquots sufficient to provide a final amount of each active component as specified in TABLE I. The synthetic metalworking fluid composition was as follows:

| COMPOSITION OF SYNTHETIC METALWORKING FLUID (pH~9) | |
| --- | --- |
| Synthetic Metalworking Fluid Ingredient | Composition Amount in Weight Percent |
| Mazer RI #4 (an amine-based corrosion inhibitor, a product of Mazer Chemical) | 6.75 |
| TP 2098 (a carboxylic acid derivative, a product of American Hoescht) | 2.25 |
| Triethanolamine (99 percent active; 1 percent H₂O) | 15.00 |
| Water | 65.00 |
| Caprylic acid (a product of Emery Chemical Co.) | 10.00 |
| Pluronic L-101 (a surfactant, a product of Rohm & Haas) | 0.50 |
| Poly-Solv ® EB (an ethylene glycol monobutyl ether, a product of Olin Corporation) | 0.50 |
| | 100.00 |

The various formulations were as follows:

TABLE I

| Formulation No. | Component Composition | Component Weight Percent | pH of Formulation | Amount of Active Component of Each Formulation Added to Synthetic Metalworking Fluid | Final pH of Synthetic Metalworking Fluid Plus Formulation |
| --- | --- | --- | --- | --- | --- |
| A | HEDP—K$_4$ (24 percent active) | 60.0 | 11.9 | 828 ppm | 9.2 |
|   | Sodium OMADINE ® (40 percent active) | 40.0 |   | 920 ppm |   |
| B | HEDP—K$_4$ (24 percent active) | 60.0 | 11.0 | 966 ppm | 9.2 |
|   | Sodium OMADINE ® (40 percent active) | 35.0 |   | 920 ppm |   |
|   | EDTA—Na$_4$ | 5.0 |   | 329 ppm |   |
| C | HEDP—K$_4$ (24 percent active) | 60.0 | 11.5 | 946 ppm | 9.2 |
|   | Sodium OMADINE ® (40 percent active) | 34.3 |   | 920 ppm |   |
|   | EDTA—Na$_4$ (100 percent active) | 5.7 |   | 382 ppm |   |
| D | HEDP—Na$_4$ (28 percent active) | 60.0 | 10.2* | 1008 ppm | 9.2 |
|   | Sodium OMADINE ® | 40.0 |   | 920 ppm |   |
| E | HEDP—Na$_4$ (28 percent active) | 60.0 | 10.7 | 1008 ppm | 9.2 |
|   | Sodium OMADINE ® | 35.0 |   | 920 ppm |   |
|   | EDTA—Na$_4$ | 5.0 |   | 328 ppm |   |

Comparison F
A commercial product containing sodium pyrithione and containing a nitriloacetic acid ferric ion chelator to prevent blue color formation, added to the synthetic metalworking fluid in an amount sufficient to provide 920 ppm of sodium pyrithione.
*pH of Formulation D was 10.7 when testing at 100 ppm Fe$^{+++}$ in synthetic metalworking fluid.

In a first set of experiments, ferric ion (added as FeCl$_3$.6H$_2$O) in an amount of 50, 100, or 150 ppm, was added to an aliquot of the synthetic metalworking fluid. One of the formulations was then added and visual color changes and the presence of precipitates were noted as given in TABLE II.

TABLE II

Effectiveness of Formulations A–E and Comparison Formulation F in Reducing Blue Coloration in a Synthetic Metalworking Fluid Containing Various Levels of Ferric Iron

| Formulation No. | Fe$^{+++}$ ppm | Visual Observation |
| --- | --- | --- |
| B | 50 | Initially Lt Purple, turns to Clear Yellow in 10 seconds |
| C | 50 | Initially Blue, Clear Yellow in 15 Sec after 16 Hr same |
| D | 50 | Initially Lt. Purple, turns to Clear Yellow in 10 Seconds |
| E | 50 | Initially Lt. Purple, turns to Yellow in 10 Seconds |
| Comparison F | 50 | Initially Dk. Blue, turns to Lt. Gray in 2 min, then Yellow/Gray after one hour, then to Clear Yellow after 16 hr |
| A | 100 | Initially Dk. Purple, turns to Clear Yellow in 30 Seconds |
| B | 100 | Initially Dk. Purple, turns to Clear Yellow in 25 Seconds |
| C | 100 | Initially Dk. Purple, turns to Clear Yellow in 30 Seconds |
| D | 100 | Initially Lt. Purple, turns to Clear Yellow in 25–30 Seconds |
| Comparison F | 100 | Dk. Purple turns to Purple/Gray after 4 hr, then to clear Dk. Yellow standing overnight noticeable precipitate |
| A | 150 | Initially Dk. Purple, turns to Clear Yellow in 1 min |
| C | 150 | Initially Dk. Purple, turns to Clear Yellow in 1 min |
| D | 150 | Initially Clear Purple, turns to Yellow in 30 Seconds |
| E | 150 | Initially Clear Purple, turns to Yellow in 30 Seconds |
| Comparison F | 150 | Initially Dk. Purple, turns to Purple/Gray After 4 hr, then to Clear Dk. Yellow after standing overnight noticeable precipitate. |

On the basis of the visual observation tests given in TABLE II, it is readily apparent that Formulations A through E generally provide superior blue color reduction as compared to Comparison Formulation F at each of the three ferric ion levels (50 ppm, 100 ppm, and 150 ppm) in the synthetic metalworking fluid tested. In addition, none of the Formulations A through F formed a precipitate in the synthetic metalworking fluid upon standing over one night, whereas the synthetic metalworking fluids containing 100 ppm and the one containing 150 ppm of ferric ion plus Comparison Formulation F each formed noticeable precipitate upon standing overnight.

A second set of experiments was run using the same formulations, synthetic metalworking fluid, and ferric ion levels as described above. However, calcium ion ($Ca^{++}$) was added to simulate a hard water-containing metalworking fluid. Calcium ion was present in the synthetic metalworking fluid at the levels described in TABLE III below, and the visual observations for these fluids are given in TABLE III.

TABLE III

Effectiveness of Formulations A Through E
And Comparison Formulation F in Reducing
Blue Coloration in a Synthetic Metalworking Fluid
Containing Various Levels of Iron and Calcium

| Formulation No. | $Fe^{+++}$ ppm | $Ca^{++}$ ppm | Observation |
|---|---|---|---|
| A | 50 | 216 | Initially Dk. Purple, turns to Clear Yellow in 30 Sec |
| C | 50 | 216 | Initially Clear Blue, turns to Yellow in 20 Sec/16 Hr same |
| Comparison F | 50 | 216 | Dk. Purple after 16 Hr |
| A | 100 | 216 | Initially Dk. Purple, turns to Yellow/Gray in 1.5 min |
| C | 100 | 216 | Initially Dk. Purple, turns to Clear Yellow in 40 seconds |
| Comparison F | 100 | 216 | Dk. Purple after 2 days Noticeable Precipitation |
| A | 150 | 216 | Initially Dk. Purple, Purple after 2 days, turns to clear yellow on standing Slight Precipitation |
| C | 150 | 216 | Initially Dk. Purple, Purple after 2 days, turns clear yellow on standing Slight Precipitation |
| Comparison F | 150 | 216 | Initially Dk. Purple turns Purple in 2 days to clear, Dk. amber on standing Heavy Precipitate |
| C | 50 | 36 | Initially clear blue, turns to Yellow in 20 Sec/16 Hr |
| Comparison F | 50 | 36 | Initially Dk. Purple, turns to Lt. Purple after 2 min, then to Gray/Yellow after 16 hr |

The results as given in TABLE III show the superior performance of Formulations A and C, as compared to Comparison Formulation F at 100 ppm and 150 ppm ferric ion and 216 ppm calcium ion based upon visual observations over a two-day period. At 100 ppm $Fe^{+++}$ and 216 ppm $Ca^{++}$, Formulation C provided a quicker clearing of the synthetic metalworking fluid to its natural yellow color than did Formulation A, apparently due to the calcium ion chelating ability of the EDTA present in Formualtion C (but not in Formualation A).

EXAMPLE 2

Efficacy of $HEDP-Na_4$ in Eliminating Blue Coloration Caused by The Presence of Ferric Ion in Pyrithione-Containing Synthetic Metalworking Fluids As a further example, the tetrasodium salt of HEDP was prepared using the set-up and procedure described in EXAMPLE 1, but by reacting NaOH with HEDP at a 90° C. reaction temperature to give a final pH of neutralization of about 11.5.

Formulations analogous to those described in EXAMPLE 1 (but replacing the $HEDP-K_4$ with identical amounts of $HEDP-Na_4$) were prepared and added to aliquots of the synthetic metalworking fluid described in EXAMPLE 1. Ferric ion was also added to the aliquots of the synthetic metalworking fluid in an amount of 50 ppm, 100 ppm, or 150 ppm.

Performance of the $HEDP-Na_4$ were comparable to that provided in EXAMPLE 1 by $HEDP-K_4$. All test fluids cleared to a clear yellow natural coloration in less than one minute.

What is claimed is:

1. A process for reducing or inhibiting the formation of a blue coloration in a metalworking fluid, said blue coloration being due to the presence of ferric ion and sodium pyrithione in said metalworking fluid, which comprises adding to said metalworking fluid an effective amount of an alkali metal or alkaline earth metal salt of 1-hydroxyethane-1,1-diphosphonic acid.

2. The process of claim 1 wherein said sodium pyrithione is present in an amount of at least about 45 ppm in said metalworking fluid and wherein said alkali metal or alkaline earth metal salt of 1-hydroxyethane-1,1-diphosphonic acid is present in said metalworking fluid in an effective amount of between about 33 and about 75 weight percent based on the total amount of said salt of 1-hydroxyethane-1,1-diphosphonic acid plus acid sodium pyrithione in said metalworking fluid.

3. The process of claim 2 wherein said alkali metal or alkaline earth metal salt of 1-hydroxyethane-1,1-diphosphonic acid is $HEDP-K_4$.

4. The process of claim 1 wherein the amount of said ferric ion dissolved in said metalworking fluid is no greater than about 150 ppm.

5. A process for reducing or inhibiting the formation of a blue coloration in an aqueous concentrate of a metalworking fluid, said blue coloration being due to the presence of ferric ion and sodium pyrithione in said aqueous concentrate, which comprises adding to said aqueous concentrate an effective amount of an alkali metal or alkaline earth metal salt of 1-hydroxyethane-1,1-diphosphonic acid, the amount of said sodium pyrithione in said aqueous concentrate being between about 450 ppm and about 5000 ppm.

6. The process of claim 5 wherein said alkali metal or alkaline earth metal salt of 1-hydroxyethane-1,1-diphosphonic acid is present in said metalworking fluid in an effective amount of between about 33 and about 75 weight percent based on the total amount of said salt of 1-hydroxyethane-1,1-diphosphonic acid plus said sodium pyrithione in said metalworking fluid.

7. The process of claim 6 wherein said alkali metal or alkaline earth metal salt of 1-hydroxyethane-1,1-diphosphonic acid is $HEDP-K_4$.

8. In an improved metalworking fluid composition containing ferric ion and sodium pyrithione, the improvement comprising said composition additionally containing an alkali metal or alkaline earth metal salt of 1-hydroxyethane-1,1-diphosphonic acid in an amount sufficient to inhibit or prevent any blue coloration in said metalworking fluid caused by the presence of said ferric ion and said sodium pyrithione.

9. The composition of claim 8 wherein said sodium pyrithione is present in an amount of at least about 45 ppm in said composition and wherein said alkali metal or alkaline earth metal salt of 1-hydroxyethane-1,1-diphosphonic acid is present in said composition in an effective amount of between about 33 and about 75 weight percent based on the total amount of said salt of 1-hydroxyethane-1,1-diphosphonic acid plus said sodium pyrithione in said metalworking fluid.

10. The comosition of claim 9 wherein said alkali metal or alkaline earth metal salt of 1-hydroxyethane-1,1-diphosphonic acid is HEDP-K$_4$.

11. The composition of claim 8 which is an aqueous concentrate containing between about 450 and about 5000 ppm of said sodium pyrithione.

12. The composition of claim 11 wherein said alkali metal or alkaline earth metal salt of 1-hydroxyethane-1,1-diphosphonic acid is present in said metalworking fluid in an effective amount of between about 33 and about 75 weight percent based on the total amount of 1-hydroxyethane-1,1-diphosphonic acid and said sodium pyrithione in said metalworking fluid.

13. The composition of claim 12 wherein said alkali metal or alkaline earth metal salt of 1-hydroxyethane-1,1-diphosphonic acid is HEDP-K$_4$.

* * * * *

UNITED STATES PATENT AND TRADEMARK OFFICE
CERTIFICATE OF CORRECTION

PATENT NO. : 4,818,436

DATED : April 4, 1989

INVENTOR(S) : French et al

It is certified that error appears in the above—identified patent and that said Letters Patent is hereby corrected as shown below:

In column 8, at line 23 after "plus" and before "so-" delete "acid" and insert --said--.

Signed and Sealed this

Sixteenth Day of June, 1992

Attest:

DOUGLAS B. COMER

*Attesting Officer*      *Acting Commissioner of Patents and Trademarks*